US00PP25608P3

(12) United States Plant Patent
Olesen et al.

(10) Patent No.: US PP25,608 P3
(45) Date of Patent: Jun. 2, 2015

(54) *CLEMATIS* PLANT NAMED 'EVIPO040'

(50) Latin Name: *Clematis viticella*
Varietal Denomination: Evipo040

(75) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 198 days.

(21) Appl. No.: 13/507,029

(22) Filed: May 31, 2012

(65) Prior Publication Data

US 2013/0326778 P1 Dec. 5, 2013

(51) Int. Cl.
*A01H 5/00* (2006.01)

(52) U.S. Cl.
USPC ..... Plt./228

(58) Field of Classification Search
USPC ..... Plt./228
CPC ..... A01H 5/02; A01H 5/00
See application file for complete search history.

(56) References Cited

PUBLICATIONS

Erwin et al. Factors Affecting Propagation of *Clematis* by Stem Cuttings. HortTechnology Oct.-Dec. 1997 7(4), 408-410.*
Rice. Raymond Evison *Clematis*—New at Chelsea '09—Graham Rice's New Plants Blog, retrived on Jan. 28, 2014, retrieved from the Internet at <http://mygarden.rhs.org.uk/blogs/graham_rice/archive/2009/05/19/raymond-evison-clematis-new-at-chelsea-09.aspx> 2 pp.*

* cited by examiner

*Primary Examiner* — June Hwu

(57) ABSTRACT

A new *Clematis* plant with a compact growth habit, profuse, violet blue flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo040'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1994 and the resulting seeds were planted the following winter in a controlled environment in Guernsey, Channel Islands. The new variety named 'Evipo040' originated as a single seedling from the stated cross.

The new *clematis* plant may be distinguished from its female seed parent and male pollen parent primarily by flower color and growth habit.

The objective of the hybridization of this *clematis* plant was to create a new and distinct variety for nursery culture with unique qualities such as:

1. Uniform and abundant violet blue flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo040' was selected by Mogens N. Olesen and Raymond J. Evison in their *clematis* development program in the Channel Islands, United Kingdom in 1995. Asexual reproduction of 'Evipo040' by means of vegetative cuttings and traditional layering was first performed by Mogens N. Olesen and Raymond J. Evison in the nursery located Channel Islands, United Kingdom during the summer of 1995. This initial and subsequent asexual propagations have demonstrated that the characteristics of 'Evipo040' are true to type and are transmitted from one generation to the next.

BRIEF DESCRIPTION OF THE DRAWINGS

The accompanying color illustrations show as true as is reasonably possible to obtain in color photographs of this type the typical characteristics of the buds, flowers, leaves, and stems, of 'Evipo040'.

Specifically illustrated in FIG. 1 are open flowers, upper and lower surface with detached tepals.

Figure 1:
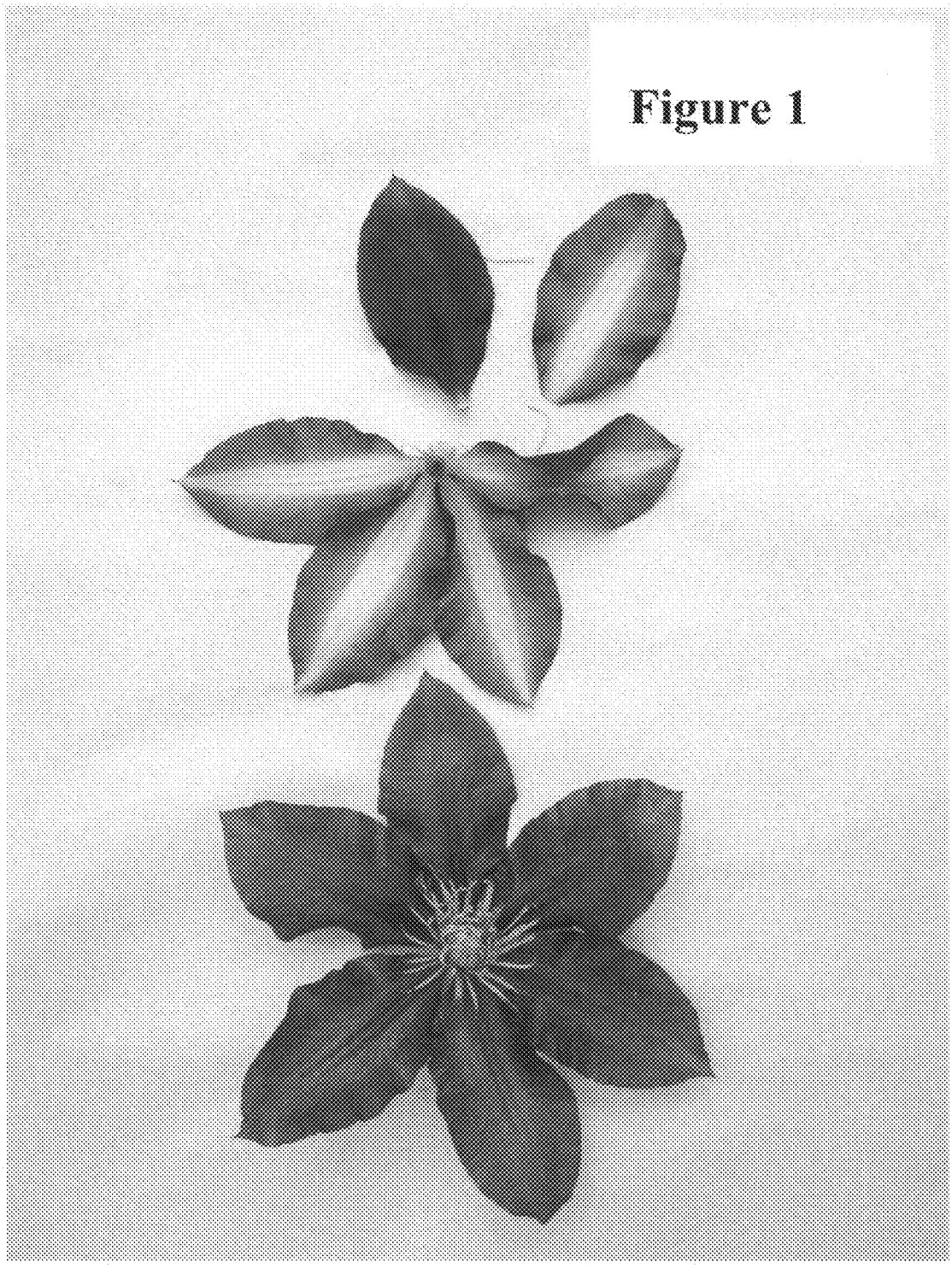
Figure 2:
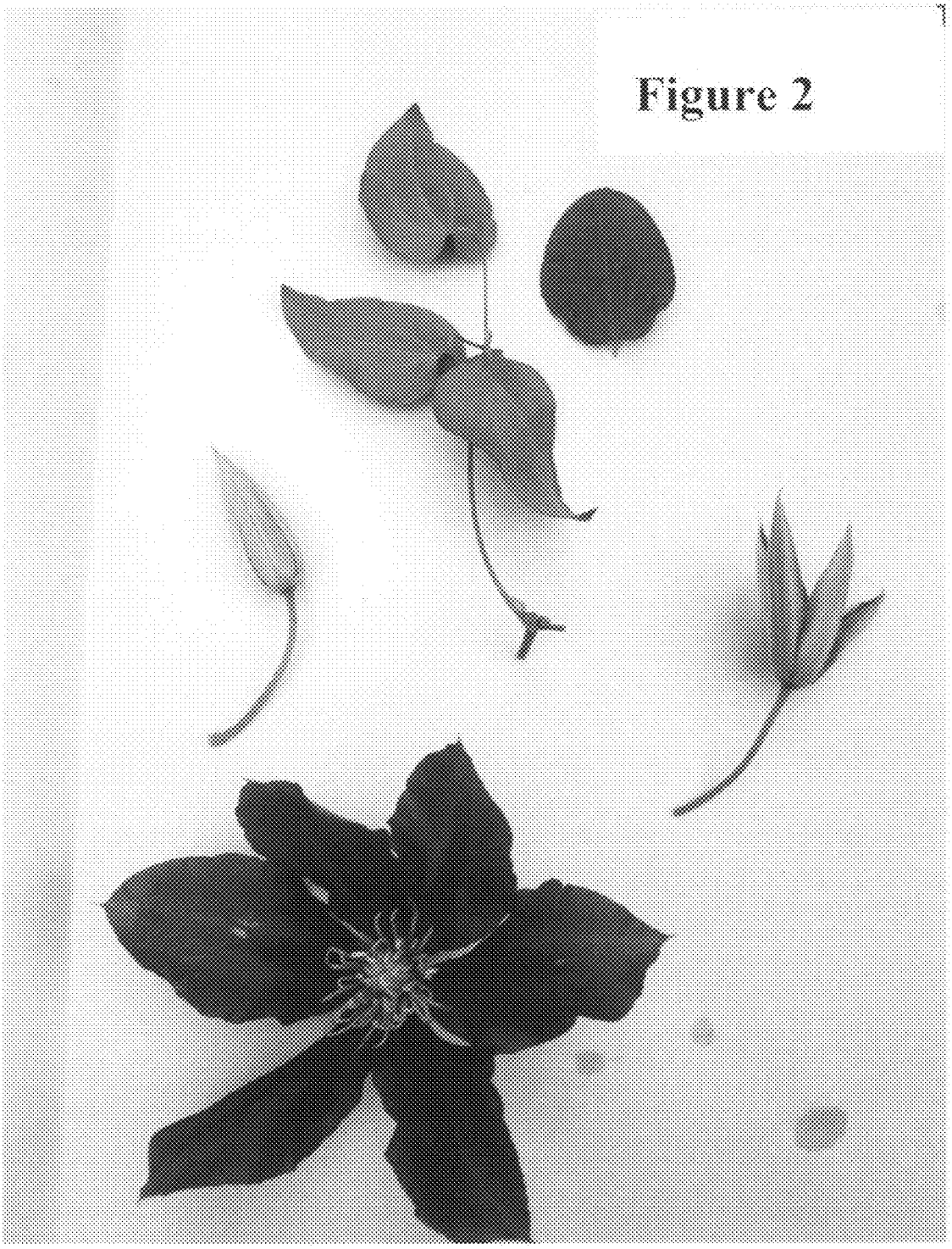
In FIG. 2 are Flower bud before opening and upon opening, detached compound leaf, and open flower.
Figure 3:
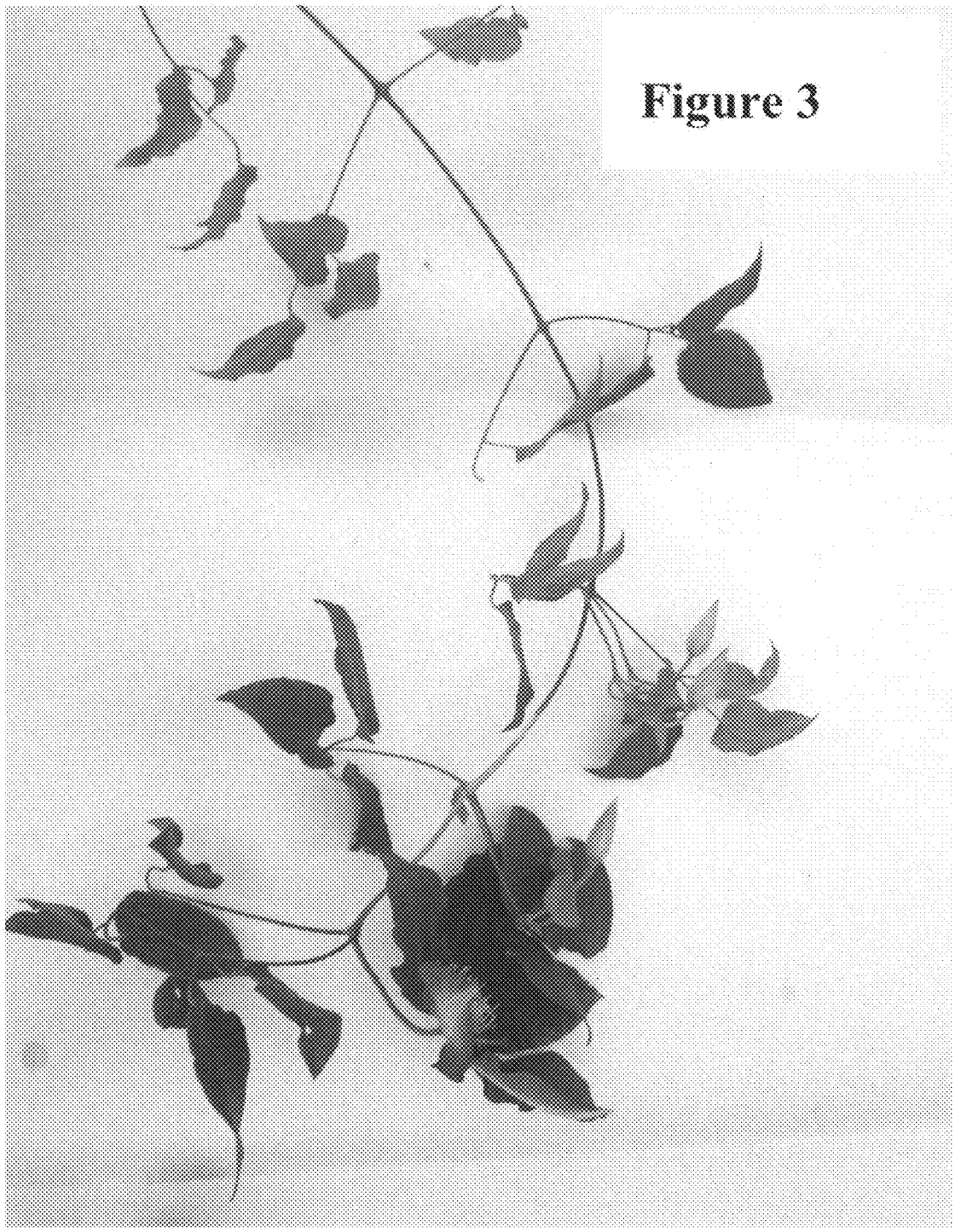
In FIG. 3 is a flowering stem showing leaf attachment and flower aspect.

Illustrated plants are 2 years of age.

DETAILED DESCRIPTION OF THE VARIETY

The following is a detailed description of 'Evipo040', as observed in its growth throughout the flowering period in glasshouses in the Channel Islands, United Kingdom. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo037' described and illustrated in U.S. Plant Pat. No. 18,104 are compared to 'Evipo040' in Chart 1.

CHART 1

| | 'Evipo040' | Evipo037 |
|---|---|---|
| Flower diameter | 150 mm | 130 to 150 mm |
| Tepal color on upper suface of open blooms | Violet Group 90B with a central bar reaching half way to the apex, the color of Purple Group N79B. | Violet-Blue Group N89D |
| Tepal count | 6 | 6 to 7 |

FLOWER AND FLOWER BUD

Blooming habit: Continuous. The natural flowering period is generally from May to September.

Flower bud:

*Size*.—Normally 30 to 50 mm in length. Bud diameter is 7 to 12 mm.

*Bud form*.—Elliptic and broad based.

*Bud color*.—Yellow Green 145C with Greyed-Purple Group 185A at the apex of the closed bud. At ¼ opening Yellow-Green Group 145C with Violet Group 86C.

Peduncle:

*Surface texture*.—Smooth, pubescent.

*Length*.—On average 25 mm.

*Diameter*.—2 mm.

*Color*.—Yellow-Green Group 144A.

*Strength*.—Moderately strong.

Receptacle:

*Surface texture*.—Very pubescent.

*Shape*.—Funnel.

*Size*.—2 mm (h)×mm 6(w).

*Color*.—Yellow-Green Group 144A.

Flower arrangement:

*Location on vine*.—New and old growth.

*Attitude*.—Flowers are turned upward at a 45 degree angle.

*Borne*.—Singly.

*Arrangement*.—Flowers overlap on the vine.

Flower bloom:

*Size*.—On average, flowers are 150 mm in diameter and 25 mm in depth.

*Profile*.—The upper side is flat. The lower side is convex.

*Fragrance*.—None.

*Flower type*.—Single.

*Lasting quality*.—Flowers normally remain 7 to 10 days on the plant.

Tepals:

*Tepal color*.—Upon opening, the upper surface is Violet Group 86B with light intonations of Purple Group 77B. Reverse side is Violet Group N88B with a central bar on the back Yellow Green Group 145A. After opening, the upper surface is Violet Group 90B with a central bar reaching half way to the apex, the color of Purple Group N79B. Reverse Violet Group N88C with a central bar the color of Green White Group 157B.

*Quantity*.—Normally 6 tepals.

*Size*.—75 mm in length by 35 mm wide.

*Shape*.—Individual tepal shape is elliptic. The tepal apex is acuminate. The tepal base is acute.

*Apex recurvature*.—Slightly recurved.

*Tepal cross section*.—Flat.

*Margins*.—Entire. Very weak undulations of margin observed.

*Persistence*.—Tepals drop off cleanly.

Reproductive organs:

*Arrangement*.—Open.

*Pollen*.—None observed.

*Anthers*.—Size: 5 mm in length. Color: White Group 155A. Quantity: About 50.

*Filaments*.—Color: Yellow-Green Group 154C at the flower central whorl of filaments. The outer whorl filaments are Green White Group 157D. Length: 10 mm.

*Pistils*.—Quantity: 40 on average.

*Stigmas*.—Protruding from the inner whorl of anthers.

*Styles*.—Color: Green White Group 157C. Length: 18 mm.

Seed head: Not observed.

PLANT

Plant form: Climbing.

Plant growth: Moderately vigorous.

Size: Seasons growth attains 1 to 1.5 meters in height. Average spread is 75 cm.

Hardiness: Trials to date show the variety hardy in USDA Zones 4-9.

Stems:

*Color*.—Juvenile stems are Yellow-Green Group 145C with anthocyanin the color of Greyed-Red Group 178B. Mature stems are Greyed-Orange Group 166B to 166C.

*Internodes*.—On average, 7 cm between nodes.

*Length*.—Normally 40 cm from the base of the plant to the flowering portion of the stem.

*Diameter*.—About 3 mm.

*Texture*.—Mature stems are ribbed. Juvenile stems are smooth.

Plant foliage:

*Leaf characteristics*.—Deciduous.

*Arrangement*.—Ternate.

*Leaf size*.—Compound leaves are normally 170 mm (l)×130 mm (w). Average terminal leaflets are normally 60 mm (l)×35 mm (w).

*Abundance*.—On average leaves per 10 cm of stem.

*Leaf color*.—Juvenile upper Yellow-Green Group 144A. Juvenile lower Yellow-Green Group 146C. Mature upper Yellow-Green Group 146A. Mature lower Yellow-Green Group 146C.

*Stipules*.—Absent.

*Petioles*.—Size: Normally 85 mm in length by 1.5 mm diameter. Texture: Smooth, lightly pubescent. Color: Yellow-Green Group N144B with intonations of Greyed-Orange Group 176C.

*Petioloule*.—Size: Terminal leaflets are attached to petioloules normally 40 mm in length by 1.5 mm diameter. Lateral petioloules are 12 mm in length by 1.5 mm diameter. Texture: Smooth and pubescent. Color: Yellow-Green Group N144B with intonations of Greyed-Orange Group 176C.

*Leaflet shape*.—Generally cordate. The apex is rounded and the base shape is rounded to cordate.

*Margin*.—Entire.

*Surface*.—The upper side is smooth. The lower side is smooth.

*Thickness*.—Average.

*Glossiness*.—Moderately Glossy.

Disease resistance: Subject to any disease that normally attacks the species. However the variety is more tolerant to *clematis* wilt than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo040', substantially as described and illustrated herein, due to its abundant violet blue flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *